US006989034B2

(12) United States Patent
Hammer et al.

(10) Patent No.: US 6,989,034 B2
(45) Date of Patent: Jan. 24, 2006

(54) ATTACHMENT OF ABSORBABLE TISSUE SCAFFOLDS TO FIXATION DEVICES

(75) Inventors: Joseph J. Hammer, Bridgewater, NJ (US); Joseph H. Contiliano, Stewartsville, NJ (US); Herbert Eugene Schwartz, Fort Wayne, IN (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/159,178

(22) Filed: May 31, 2002

(65) Prior Publication Data

US 2003/0225459 A1  Dec. 4, 2003

(51) Int. Cl.
*A61F 2/36* (2006.01)
(52) U.S. Cl. .................. 623/23.72; 623/23.75
(58) Field of Classification Search ... 623/23.72–23.76
See application file for complete search history.

(56) References Cited

U.S. PATENT DOCUMENTS

| | | | |
|---|---|---|---|
| 4,060,081 A | 11/1977 | Yannas | |
| 4,186,448 A | 2/1980 | Brekke | |
| 4,927,632 A | 5/1990 | Wong | |
| 5,059,123 A | 10/1991 | Jernberg | |
| 5,067,964 A | 11/1991 | Richmond et al. | |
| 5,133,755 A | 7/1992 | Brekke | |
| 5,306,311 A | 4/1994 | Stone et al. | |
| 5,314,478 A | 5/1994 | Oka et al. | |
| 5,466,262 A | 11/1995 | Saffran | |
| 5,492,697 A | 2/1996 | Boyan et al. | |
| 5,514,378 A | 5/1996 | Mikos et al. | |
| 5,522,895 A | 6/1996 | Mikos | |
| 5,607,474 A | 3/1997 | Athanasiou et al. | |
| 5,624,463 A | 4/1997 | Stone et al. | |
| 5,629,077 A | 5/1997 | Turnlund et al. | |
| 5,632,745 A | 5/1997 | Schwartz | |
| 5,658,582 A | 8/1997 | Dorigatti et al. | |
| 5,677,355 A | 10/1997 | Shalaby et al. | |
| 5,686,311 A | 11/1997 | Shaw | |
| 5,711,960 A | 1/1998 | Shikinami | |
| 5,713,374 A | 2/1998 | Pachence et al. | |
| 5,723,508 A | 3/1998 | Healy et al. | |
| 5,749,874 A | 5/1998 | Schwartz | |
| 5,755,792 A | 5/1998 | Brekke | |
| 5,769,899 A | 6/1998 | Schwartz et al. | |
| 5,770,193 A | 6/1998 | Vacanti et al. | |
| 5,899,939 A | 5/1999 | Boyce et al. | |

(Continued)

FOREIGN PATENT DOCUMENTS

EP  274849  8/1991

(Continued)

OTHER PUBLICATIONS

U.S. Appl. No. 10/154,136, Ethicon, Inc.

(Continued)

*Primary Examiner*—Thomas C. Barrett

(57) ABSTRACT

The present invention relates to tissue scaffold implant devices useful in the repair and/or regeneration of diseased and/or damaged musculoskeletal tissue and that include a tissue scaffold component fixedly attached to a scaffold fixation component via at least one of sutures, fabrics, fibers, threads, elastomeric bands, reinforcing elements and interlocking protrusions for engaging and maintaining the scaffold component fixedly attached to the fixation component.

9 Claims, 6 Drawing Sheets

U.S. PATENT DOCUMENTS

| | | |
|---|---|---|
| 5,972,385 A | 10/1999 | Liu et al. |
| 6,031,148 A | 2/2000 | Hayes et al. |
| 6,075,180 A | 6/2000 | Sharber et al. |
| 6,143,293 A * | 11/2000 | Weiss et al. ............... 424/93.7 |
| 6,306,424 B1 | 10/2001 | Vyakarnam et al. |
| 6,333,029 B1 | 12/2001 | Vyakarnam et al. |
| 6,355,149 B1 | 3/2002 | Vyakarnam et al |
| 6,365,149 B2 | 4/2002 | Vyakarnam et al. |
| 6,454,811 B1 | 9/2002 | Sherwood et al. |
| 6,626,950 B2 | 9/2003 | Brown et al. |
| 2001/0008980 A1 | 7/2001 | Gresser |
| 2002/0119177 A1 * | 8/2002 | Bowman et al. ............ 424/423 |
| 2002/0120348 A1 | 8/2002 | Melican et al. |

FOREIGN PATENT DOCUMENTS

| | | |
|---|---|---|
| EP | 1064958 | 1/2001 |
| WO | WO 97 45532 | 12/1997 |
| WO | WO 99 47186 | 9/1999 |
| WO | WO 00/74554 A2 * | 9/2000 |
| WO | WO 01 10306 | 2/2001 |

OTHER PUBLICATIONS

U.S. Appl. No. 09/874,218, Ethicon, Inc.

* cited by examiner

ATTACHMENT OF ABSORBABLE TISSUE SCAFFOLDS TO FIXATION DEVICES

FIELD OF THE INVENTION

The present invention relates to bioabsorbable tissue scaffold implant devices that facilitate repair or regeneration of diseased or damaged musculoskeletal tissue.

BACKGROUND OF THE INVENTION

Tissue engineering (TE) is the application of engineering disciplines to either maintain existing tissue structures or to enable new tissue growth. This engineering approach generally includes the delivery of a biocompatible tissue scaffold that serves as an architectural support onto which cells may attach, proliferate, and synthesize new tissue to repair a wound or defect. Preferably, the tissue scaffolds should be made of bioabsorbable materials. Bioabsorbable tissue scaffolds are absorbed by the body after the body has synthesized new tissue to repair the wound or defect. Synthetic bioabsorbable biocompatible polymers are well known in the art and include aliphatic polyesters, homopolymers, and copolymers (random, block, segmented and graft) of monomers such as glycolic acid, glycolide, lactic acid, lactide (d, l, meso and mixtures thereof), $\epsilon$-caprolactone, trimethylene carbonate and p-dioxanone.

Many absorbable tissue scaffolds have been recognized for use in the repair and regeneration of tissue. Porous mesh plugs composed of polyhydroxy acid polymers such as polylactide are used for healing bone voids. More recently, other tissue engineering scaffolds have been reported. These scaffolds are manufactured by a number of different processes, including the use of leachables to create porosity in the scaffold, vacuum foaming techniques and precipitated polymer gel masses. Polymer melts with fugitive compounds that sublimate at temperatures greater than room temperature are known. Textile-based, fibrous tissue scaffolds and biocompatible, bioabsorbable foam tissue scaffolds formed by lyophilization are known. A porous, open-cell foam of polyhydroxy acids with pore sizes from, about 10 to about 200 $\mu$m is used for the in-growth of blood vessels and cells. The foam also could be reinforced with fibers, yarns, braids, knitted fabrics, scrims and the like.

Articular cartilage is a tissue that covers the articulating surfaces between bones in the joints and consists of two principal phases: a solid matrix and an interstitial fluid phase. The matrix, which gives cartilage its stiffness and strength is produced and maintained by chondrocytes. The interstitial fluid phase provides viscoelastic behavior to the cartilage tissue. In repairing articular cartilage, the tissue engineering scaffold must be fastened to the underlying bone so as not to be displaced by the movement of the joint.

Methods of repairing articular cartilage are known. One known articular cartilage repair piece includes a backing layer of non-woven, felted fibrous material which is either uncoated or covered by a coating of tough, pliable material. Means for fastening the repair piece to the underlying bone include elongated fasteners, suturing, adhesive bonding, and mechanical interlocking in an undercut portion of bone.

One attachment method to hold a biomaterial in place until healing occurs includes several steps. First, sutures are anchored through the subchondral plate into bony tissue with at least two lines emerging from the surface. The two lines are then pulled through the implant and used to secure the cartilage repair materials in place.

To avoid the need for a multi-step process, several prior works describe devices that combine scaffolds and the means for fastening the scaffolds to the underlying bone. For example, in one known prosthetic, resorbable, articular cartilage scaffold, an absorbable base component is adapted for insertion into a pilot hole into cancellous bone, permitting anchoring of the device into that bone. The scaffold is fabricated of biocompatible, bioresorbable fibers. In forming the device, some of the fibers in the scaffold are compressively forced through holes in the top of the base component to attach the scaffold to the base. This compressive force, used to attach the scaffold to the base, may damage the scaffold.

In another known bioabsorbable cartilage repair system, a porous bioabsorbable insert is held in the side walls of a support frame by means of radially, outwardly-extending flanges that pass through windows in the side walls. Though this results in a single device combining a scaffold and a means for fastening the scaffolds to underlying bone, the scaffold must be manufactured to contain the radially, outwardly-extending flanges.

Biocompatible tissue scaffolds also have been prepared from biological-based polymers such as hyaluronic acid (HA), collagen, alginates, chitosan, small intestine submucosa (SIS) and blends thereof. Three-dimensional porous foams and nonwoven structures of various biopolymers such as HA and collagen are known.

There are a number of tissue engineered scaffold devices that serve as architectural supports for the growth of new tissue structures. Although means for fastening these devices to the underlying bone have been described, the limits on the previously disclosed methods and devices include the need for a multistep fastening process, possible damage to the scaffold, and scaffolds that must be manufactured in very specific shapes to attach to the fastening means. Accordingly, there is a need for tissue engineering scaffold devices to be firmly affixed to hard tissue, such as bone or cartilage, wherein the scaffolds are held in place in the fixation device while tissue ingrowth occurs.

SUMMARY OF THE INVENTION

The present invention relates to tissue scaffold implant devices comprising a scaffold fixation component and a tissue scaffold component fixedly attached to the scaffold fixation component. The tissue scaffold component and the scaffold fixation component are fixedly attached one to the other via attachment means such as sutures, fibers, ties, threads and elastomeric bands. Any means equivalent in function to such attachment means also are contemplated by the present invention. Alternatively, the tissue scaffold component may be encased by a fabric that then is fixedly attached to the fixation component via attachment means as noted above. In another embodiment, a reinforcing element may be partially embedded in the scaffold component and positioned about the scaffold component to maintain the relative position of the scaffold component to the fixation component, and the unembedded portion of the reinforcing element is fixedly attached to the fixation component. In yet another embodiment, the scaffold fixation component comprises at least one interlocking protrusion for engaging the tissue scaffold component and maintaining the tissue scaffold component fixedly attached to the scaffold fixation component. The protrusions are used to fixedly attach the tissue scaffold component to the scaffold fixation component.

DETAILED DESCRIPTION OF THE INVENTION

In the repair of articular cartilage, the structure of the implant must be effective to facilitate tissue ingrowth, and the implant must have sufficient structural integrity and physical properties to facilitate ease of handling in an operating room environment. Therefore, the components comprising the implant must be fixedly attached to one another.

Figure 1:
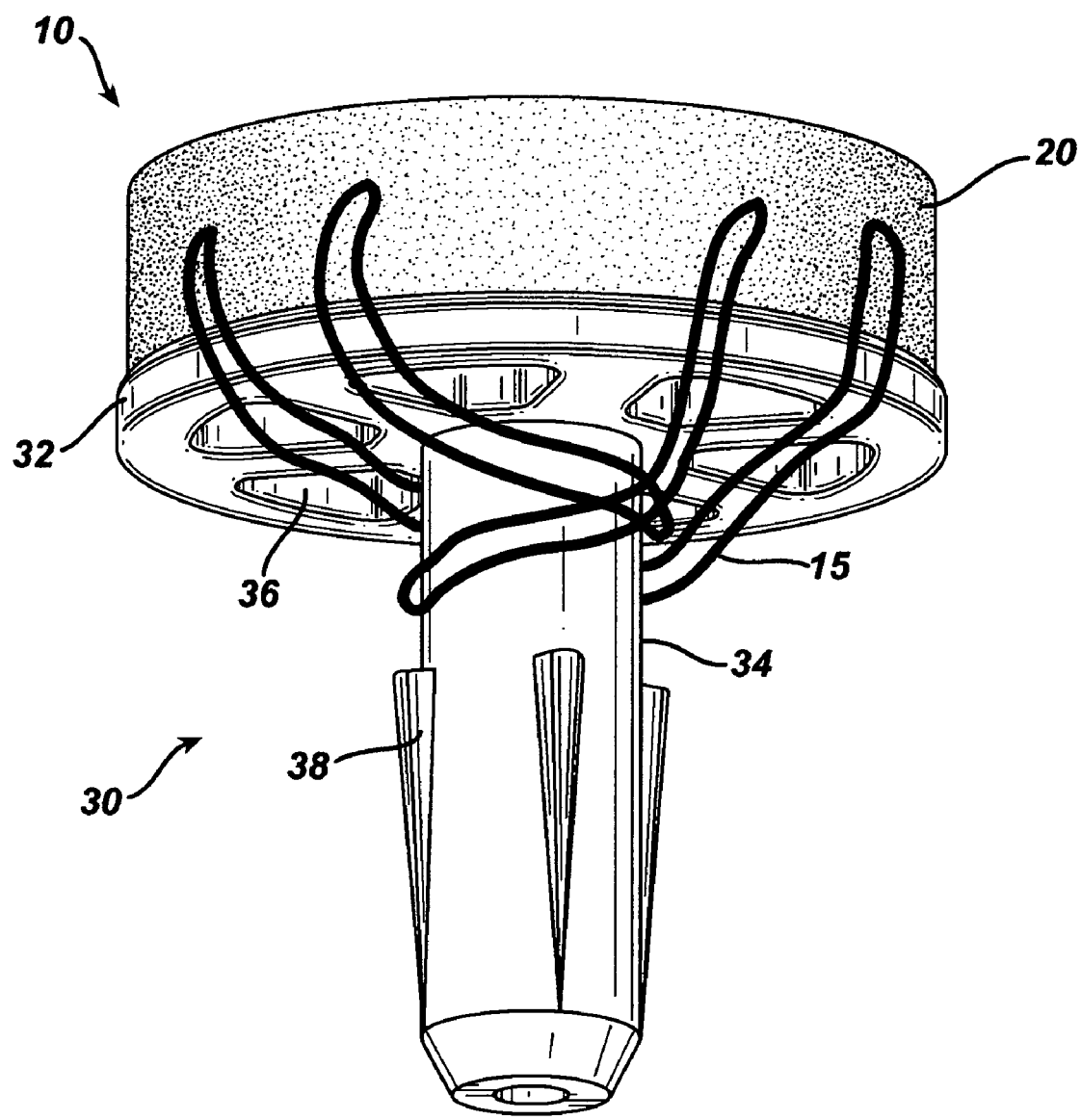
FIG. 1 is a bottom perspective view of a device of the present invention.
Figure 2:
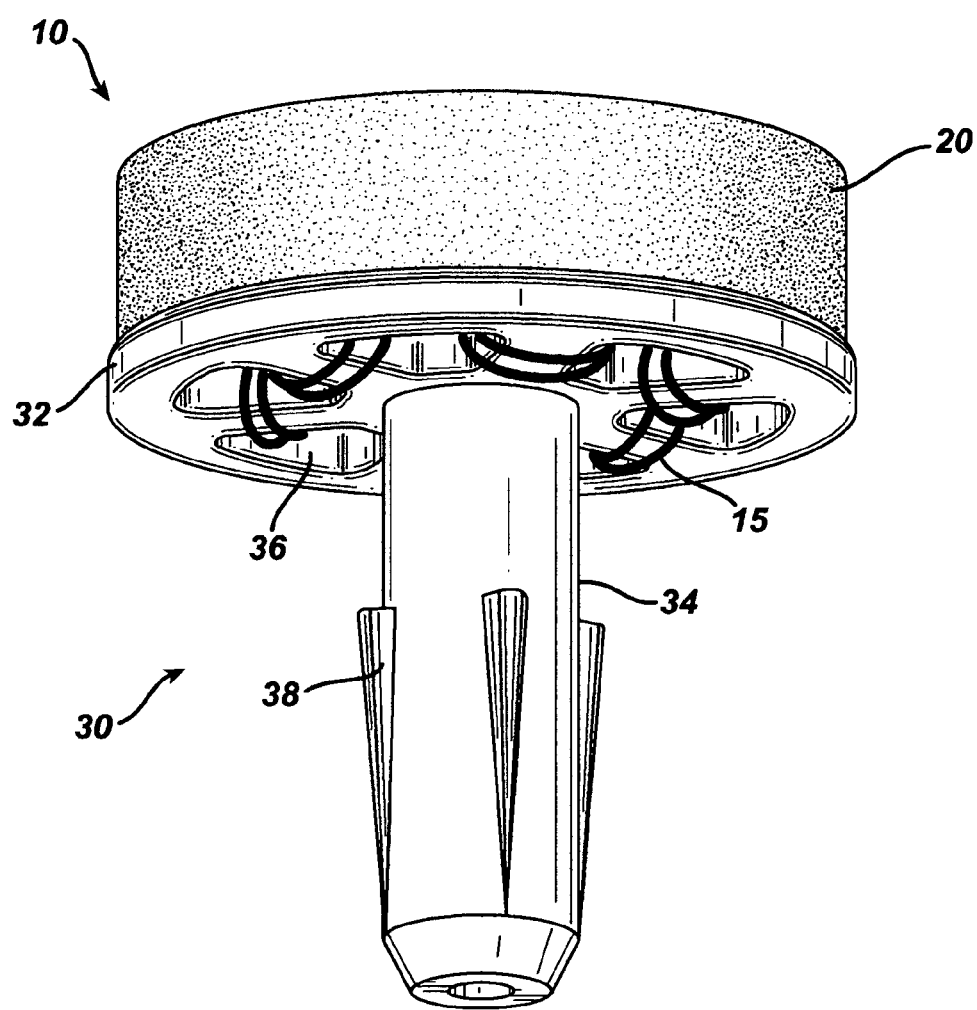
FIG. 2 is a bottom perspective view of a device of the present invention.

Referring to FIGS. 1 and 2, implant 10 includes scaffold component 20, fixation component 30, and sutures 15. Fixation component 30 includes scaffold support 32 and fixation post 34. Scaffold support 32 includes perforations 36 therethrough to allow fluid to flow to and from scaffold component 20. Preferably, fixation post 34 may contain ribs, serrations, or other surface roughness or engagement means 38 that improve attachment of anchoring post 34 to the implant site.

The design of fixation component 30 is not a crucial element of the present invention. However, in certain embodiments where securement of the scaffold to the scaffold support is effected by tying with, e.g. sutures, fibers, threads, elastomeric bands, etc., the device preferably comprises scaffold support 32 with perforations 36 therethrough. Scaffold component 20 is affixed to the top surface of scaffold support 32 via, e.g. sutures 15.

Implant 10 must have sufficient structural integrity and physical properties not only to facilitate ease of handling in an operating room environment but also to maintain the relative position of the tissue scaffold to the fixation device. Scaffold component 20 and fixation component 30 must be fixedly attached so as not to separate before, during or after the surgical procedure. Sufficient strength and physical properties are developed in the implant through the selection of materials used to form scaffold 20, fixation components 30 and sutures 15.

FIGS. 1 and 2 show tissue-engineered scaffold component 20 positioned on the top surface of scaffold support 32 of fixation component 30. FIG. 1 shows suture 15 utilized to secure scaffold component 20 to fixation component 30. The suture is sewn through scaffold 20 and attached to fixation component 30 by tying suture 15 to fixation post 34. Once tied in place, excess suture 15 is removed.

FIG. 2 shows a preferred utilization of suture 15 to secure scaffold component 20 to fixation component 30. Suture 15 is sewn through scaffold 20 and passes through perforations 36 in scaffold support 32. Once tied in place, excess suture 15 is removed.

Figure 3:
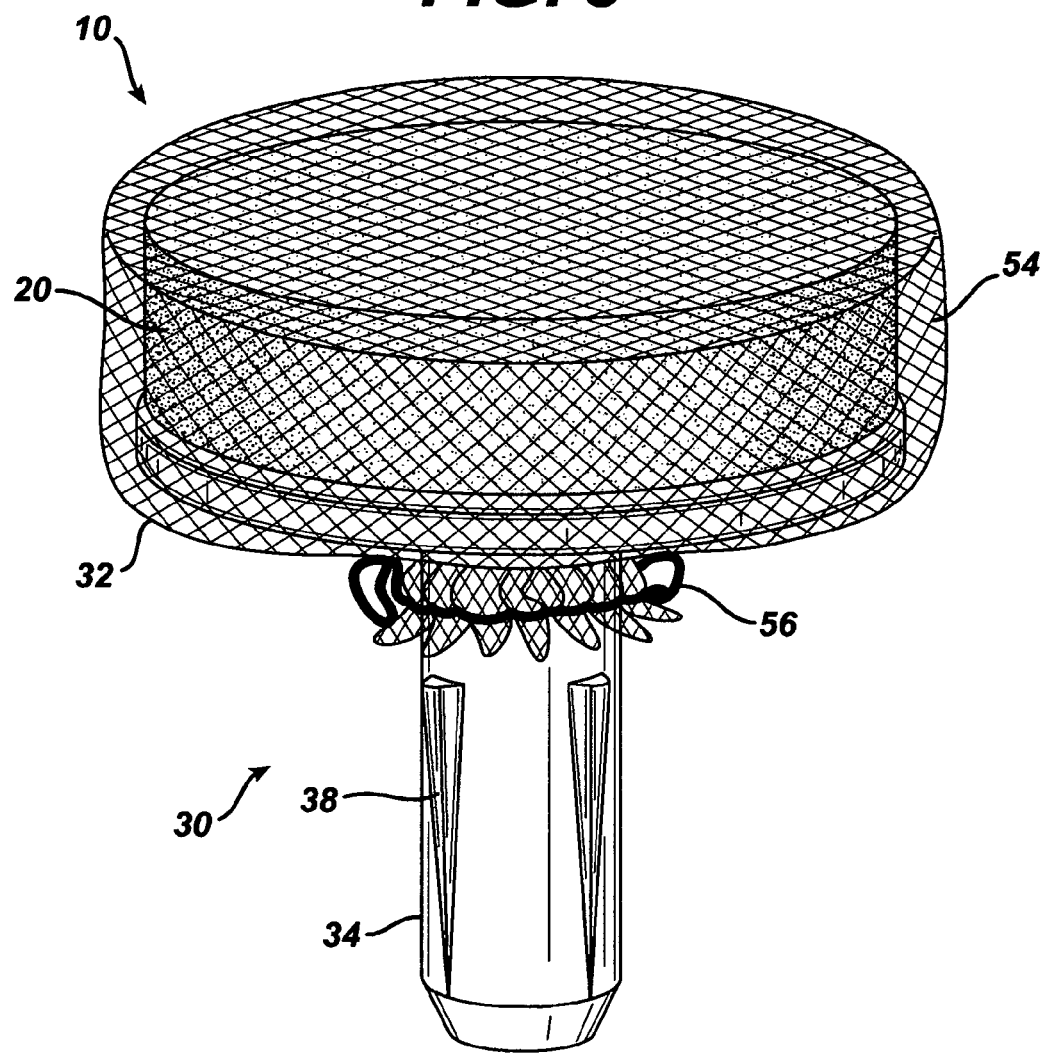
FIG. 3 is a top perspective view of a device of the present invention.

In another embodiment of the present invention, shown in FIG. 3, fabric 54 encases scaffold component 20 and scaffold support 32, and fabric 54 is attached to fixation post 34 of fixation component 30 by attachment means 56. Attachment means include sutures, fibers, threads, ties, elastomeric bands, and the functional equivalents thereof. Preferably, sutures are used as the attachment means.

Figure 4:
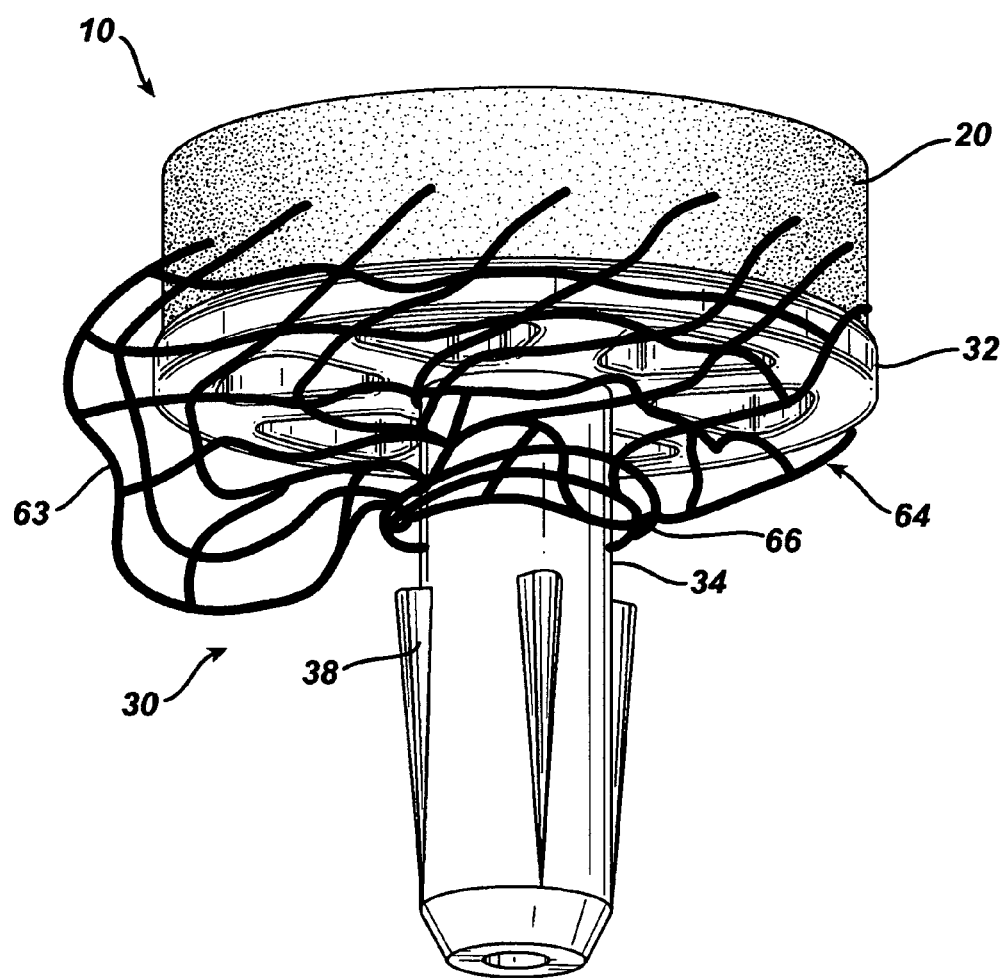
FIG. 4 is a bottom perspective view of a device of the present invention.

In yet another embodiment, shown on FIG. 4, a portion of reinforcement element 63 is positioned about and partially embedded in scaffold component 20. The unembedded portion 64 of reinforcement element 63 is attached to fixation post 34 of fixation component 30 by attachment means 66. Reinforcement element 63 may comprise fibers, yarns, braids, woven fabrics, knitted fabrics and scrims. Preferably, reinforcement element 63 comprises woven fabrics. Attachment means 66 include sutures, fibers, threads, ties, elastomeric bands, and the functional equivalents thereof. Preferably, sutures are used as the attachment means.

In this embodiment, the preferable process for simultaneously forming scaffold component 20 and embedding reinforcement element 63 in scaffold component 20 is a lyophilization, or freeze-drying, process. In brief, reinforcement element 63 is immersed in a polymer solution prior to initiation of the freeze-drying process. When scaffold component 20 is formed, reinforcement element 63 is partially embedded in place to form a fixed attachment between scaffold component 20 and reinforcement element 63. Scaffold component 20 is formed as a porous, polymeric foam scaffold.

Figure 5:
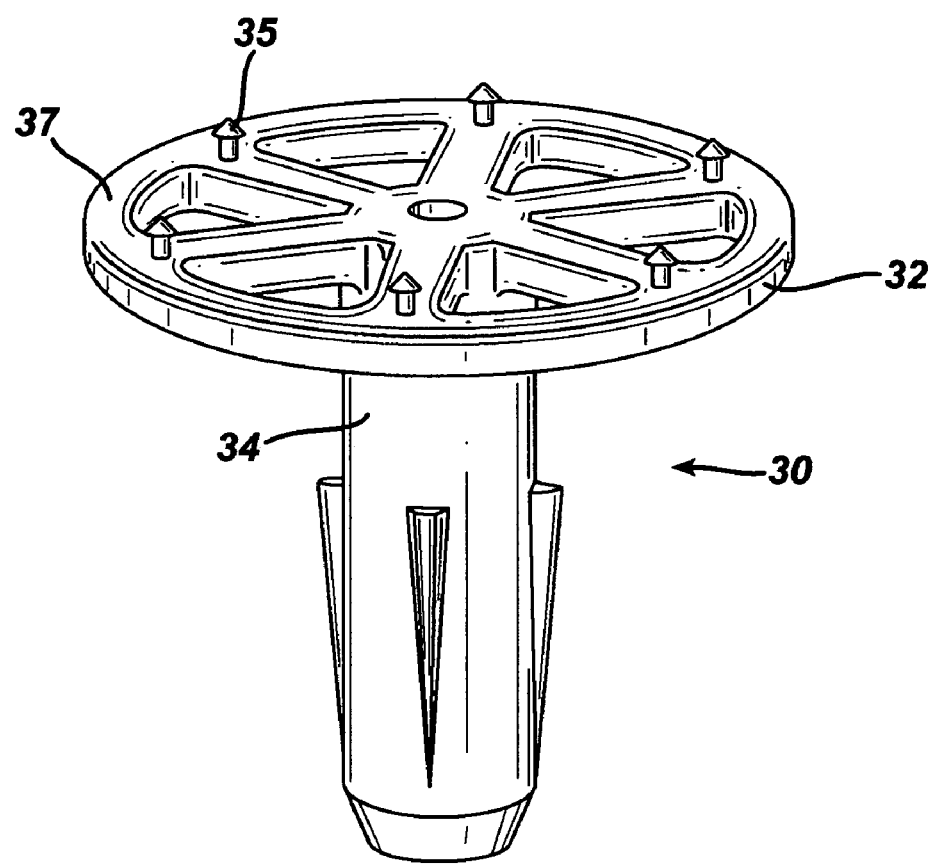
FIG. 5 is a top perspective view of a fixation component of a device of the present invention.

In another embodiment of the present invention, interlocking protrusions from the fixation device are used to secure the tissue scaffold to the fixation device. FIG. 5 shows scaffold fixation device 30, comprising scaffold support 32 and fixation post 34. Protrusions 35 are located at numerous positions on upper surface 37 of scaffold support 32.

Figure 6:
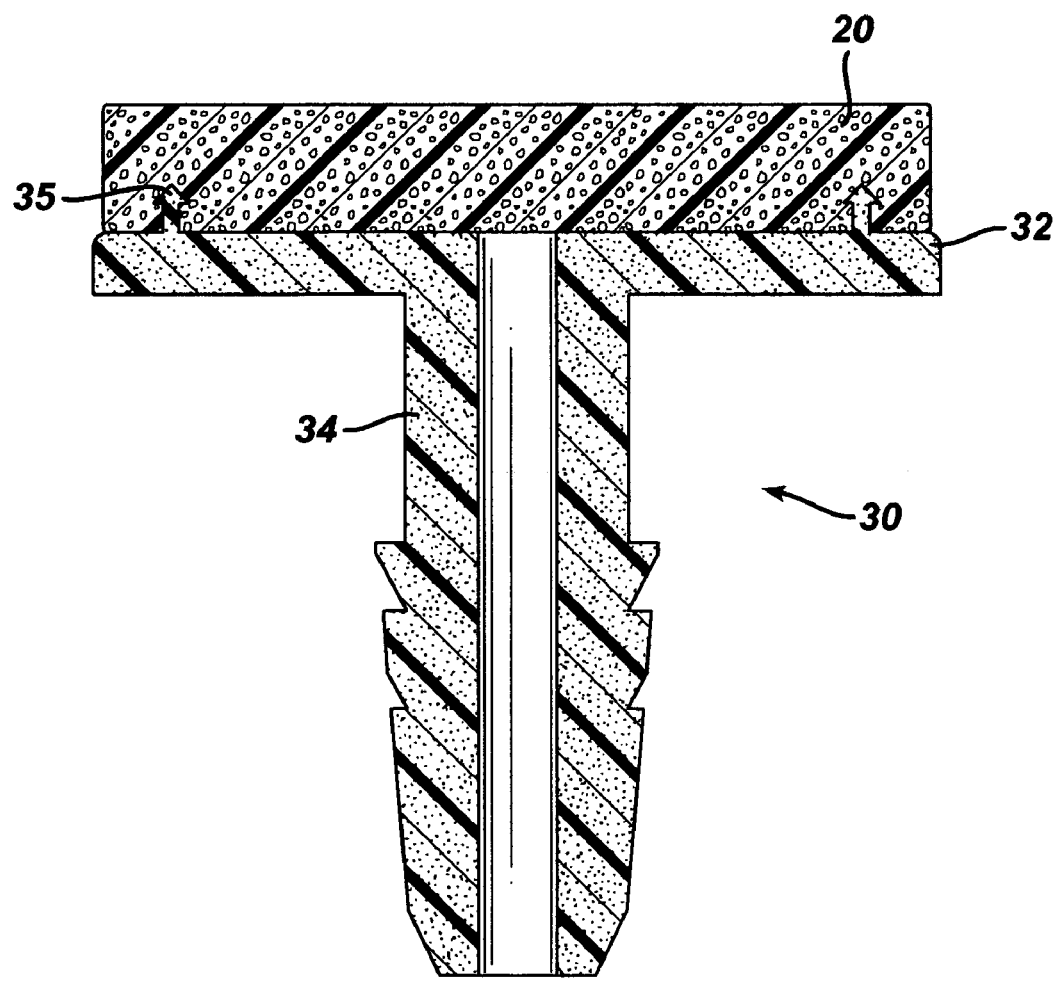
FIG. 6 is a cross section view of a device of the present invention.

As seen in FIG. 6, when scaffold 20 is placed in contact with support component 32 of fixation device 30, protrusions 35 engage tissue scaffold component 20 directly by penetrating scaffold component 20 and are securely embedded in an interlocking relationship within the body of scaffold component 20. Scaffold component 20 thus is maintained in proper position during placement by the physician. As the protrusions provide fixed attachment of the scaffold component to the scaffold support by way of penetration of the scaffold body, the scaffold component must comprise material that may be penetrated by the protrusions and in which the protrusions will remain embedded in an interlocking relationship during placement. Examples of such scaffolds include, without limitation, felt and polymeric foam scaffolds. More preferred in devices of the present invention are lyophilized, bioabsorbable foam scaffolds.

The number and geometry of the protrusions are not limited to those depicted in FIG. 5, as one skilled in the art may design a number of other geometeries for protrusions or functionally equivalent features that will penetrate and engage tissue-engineered scaffolds and maintain them in appropriate position on the scaffold support of the fixation device.

The methods of attaching scaffold component 20 and fixation component 30 discussed above may be used on a variety of the tissue-engineered scaffolds that have been reported in the art. As mentioned earlier, prior art tissue engineered scaffolds include, but are not limited to, porous mesh plugs, porous scaffolds formed by leaching, vacuum forming, or lyophilization, textile-based fibrous scaffolds and lyophilized foams reinforced with fibers, yarns, braids, knitted fabrics and scrims.

Scaffold component 20 and fixation component 30 of the invention may be composed of non-absorbable materials, such as biocompatible metals, including but not limited to stainless steel, cobalt chrome, titanium and titanium alloys; or bio-inert ceramics, including but not limited to alumina, zirconia, and calcium sulfate; or absorbable glasses or ceramics comprising calcium phosphates; or autograft, allograft, or xenograft bone tissue; or non-bioabsorbable polymers, including but not limited to polyethylene, polyvinyl alcohol (PVA), polymethylmethacrylte (PMMA), silicone, polyethylene oxide (PEO), polyethylene glycol (PEG), and polyurethanes; or biocompatible and resorbable biopolymers. As used herein, the term "biopolymer" is understood to encompass naturally occurring polymers, as well as synthetic modifications or derivatives thereof. Such biopolymers include, without limitation, hyaluronic acid, collagen, recombinant collagen, cellulose, elastin, alginates, chondroitin sulfate, chitosan, chitin, keratin, silk, small intestine submuccosa (SIS) and blends thereof. These biopolymers can be further modified to enhance their mechanical or degradation properties by introducing cross-linking agents or changing the hydrophobicity of the side residues.

In a preferred embodiment, scaffold component 20 and fixation component 30 preferably comprise bioabsorbable polymers. Such a device utilizing the method of attachment of the present invention will result in a tissue-engineered scaffold implant device that is fully absorbable by the body.

A variety of bioabsorbable polymers can be used to make tissue-engineered scaffold implant devices according to the present invention. Examples of suitable biocompatible, bioabsorbable polymers include polymers selected from the group consisting of aliphatic polyesters, polyalkylene oxalates, polyamides, polycarbonates, polyorthoesters, polyoxaesters, polyamidoesters, polyanhydrides, and polyphosphazenes.

Currently, aliphatic polyesters are among the preferred absorbable polymers for use in making the foam scaffold component according to the present invention. Aliphatic polyesters can be homopolymers or copolymers (random, block, segmented, tapered blocks, graft, triblock, etc.) having a linear, branched or star structure. Suitable monomers for making aliphatic homopolymers and copolymers may be selected from the group consisting of, but are not limited to, lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), -valerolactone, -butyrolactone, -decalactone, 2,5-diketomorpholine, pivalolactone, -diethylpropiolactone, ethylene carbonate, ethylene oxalate, 3-methyl-1,4-dioxane-2,5-dione, 3,3-diethyl-1,4-dioxan-2,5-dione, -butyrolactone, 1,4-dioxepan-2-one, 1,5-dioxepan-2-one, 6,6-dimethyl-dioxepan-2-one and 6,8-dioxabicycloctane-7-one.

The aliphatic polyesters are typically synthesized in a ring-opening polymerization. The monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

Suitable solvents that may be used in the preparation of the tissue scaffold implant include, but are not limited to, formic acid, ethyl formate, acetic acid, hexafluoroisopropanol (HFIP), cyclic ethers (i.e. THF, DMF, and PDO), acetone, acetates of $C_2$ to $C_5$ alcohol (such as ethyl acetate and t-butylacetate), glyme (i.e. monoglyme, ethyl glyme, diglyme, ethyl diglyme, triglyme, butyl diglyme and tetraglyme) methylethyl ketone, dipropyleneglycol methyl ether, lactones (such as γ-valerolactone, δ-valerolactone, β-butyrolactone, γ-butyrolactone) 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, the preferred solvent is 1,4-dioxane. A homogeneous solution of the polymer in the solvent is prepared using standard techniques.

In yet another embodiment of the present invention, the polymers and blends can be used as a therapeutic agent release matrix. To form this matrix, the polymer would be mixed with a therapeutic agent prior to forming the device. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; analgesics; growth factors, including bone morphogenic proteins (i.e. BMP's 2, 4, 6 and 12), sonic hedgehog, bone morphogenic-like proteins (i.e. GFD-5, GFD-7 and GFD-8), epidermal growth factor (EGF), fibroblast growth factor (i.e. FGF 1–9), platelet derived growth factor (PDGF), insulin like growth factor (IGF-I and IGF-II), transforming growth factors (i.e. TGF-βI-III), vascular endothelial growth factor (VEGF); and other naturally derived or genetically engineered proteins, polysaccharides, glycoproteins, lipoproteins and cells.

Matrix materials for the present invention may be formulated by mixing one or more therapeutic agents with the polymer. Alternatively, a therapeutic agent could be coated on to the polymer, preferably with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

In another embodiment, the fixation device can be fabricated from biocompatible ceramics such as hydroxyapatite, tricalcium phosphate, or blends with biocompatible and resorbable synthetic, or metal alloys. The devices could also be made from natural materials (ie allograft bone, xenograft bone, coral etc.)

The following examples are illustrative of the principles and practice of the invention, although not limiting the scope of the invention. Numerous additional embodiments within the scope and spirit of the invention will become apparent to those skilled in the art.

In the examples, the polymers and monomers were characterized for chemical composition and purity (NMR, FTIR), thermal analysis (DSC), and molecular weight by conventional analytical techniques.

Inherent viscosities (I.V., dL/g) of the polymers and copolymers were measured using a 50 bore Cannon-Ubbelhode dilution viscometer immersed in a thermostatically controlled water bath at 25° C. utilizing chloroform or hexafluoroisopropanol (HFIP) as the solvent at a concentration of 0.1 g/dL.

EXAMPLE 1

Suture Attachment of the Tissue Engineering Scaffold Component to the Fixation Component Bioabsorbable fixation components were manufactured using an injection molding process. The design of the fixation component used is the same as that depicted in FIG. 1. The polymer used to manufacture the fixation components was a copolymer of 85% PLA and 15% PGA (85/15 PLA/PGA) produced by Purac (Gorinchem, The Netherlands), with an I.V. of 1.79 dL/g as measured in chloroform. The injection molder (Niigata NN35MI) had a barrel diameter of 18 mm. The hopper was fitted with a nitrogen purge to keep the polymer dry. The feed, transition and compression zone temperatures were 185° C., 185° C. and 191° C., respectively. The die and mold temperatures were 191° C. and 24° C., respectively. The maximum injection speed was 80 mm/s and maximum injection pressure was 85 Kgf/cm$^2$. The hold pressure was 70 Kgf/cm$^2$. The total time for injection and hold was 3 seconds and the cooling time at the end of hold cycle was 20 seconds. The resulting fixation components had scaffold supports that were seven millimeters in diameter.

Scaffold components were made as described below. A copolymer of PGA/PLA (90/10) was melt extruded into continuous multifilament yarn by conventional methods of making yarn and subsequently oriented in order to increase strength, elongation, and energy required to rupture. The yarns comprised filaments of approximately 20 microns in diameter. These yarns were then cut and crimped into uniform 2.0 inch lengths to form 2.0 inch staple fiber.

A dry lay needle punched nonwoven matrix was then prepared utilizing the 90/10 PGA/PLA copolymer staple fibers. The staple fibers were opened and carded on standard nonwoven machinery. The resulting mat was in the form of webbed staple fibers. The webbed staple fibers were needle punched to form the dry lay needle punched nonwoven matrix, or the scaffold component.

The scaffold component was rinsed in water followed by another incubation in ethanol to remove any residual chemicals or processing aids used during the manufacturing process.

The scaffold component was attached the to the fixation component as follows. Seven millimeter diameter disks of the scaffold component were cut using a steel ruled die. Continuous braid of 90/10 PGA/PLA copolymer (filaments of approximately 20 microns in diameter) was sewn through the scaffold component and passed through perforations in the scaffold support of the fixation component. The scaffold component was thereby bonded to the fixation component.

In these examples certain abbreviations are used, such as PCL to indicate polymerized ε-caprolactone, PGA to indicate polymerized glycolide, PLA to indicate polymerized (L)lactide. Additionally, the percentages in front of the copolymer indicates the respective mole percentages of each constituent.

We claim:

1. A tissue scaffold implant device, comprising:
    a tissue scaffold component comprising a porous, lyophilized polymeric foam having reinforcing elements selected from the group consisting of fibers, yarns, braids, woven fabrics, knitted fabrics and scrims partially embedded therein; and
    a fixation component comprising a tissue scaffold support component and an anchoring post,
    wherein said tissue scaffold component is fixedly attached to said fixation component via an attachment means selected from the group consisting of fibers, sutures, ties, threads, elastomeric bands.

2. The device of claim 1 wherein said tissue scaffold component comprises a bioabsorbable polymer.

3. The device of claim 1 wherein said fixation component comprises a bioabsorbable polymer.

4. The device of claim 1 wherein said tissue scaffold component and said fixation component comprise a bioabsorbable polymer.

5. The device of claim 4 wherein said bioabsorbable polymer is selected from the group consisting of aliphatic polyesters, polyalkylene oxalates, polyamides, polycarbonates, polyorthoesters, polyoxaesters, polyamidoesters, polyanhydrides and polyphosphazenes.

6. The device of claim 5 wherein said aliphatic polyesters are selected from the group consisting of homopolymer and copolymers of lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), 2,5-diketomorpholine, pivalolactone, ethylene carbonate, ethylene oxalate, 3-methyl-1,4-dioxane-2,5-dione, 3,3-diethyl-1,4-dioxan-2,5-dione, 1,4-dioxepan-2-one, 1,5-dioxepan-2-one, 6,6-dimethyl-dioxepan-2-one and 6,8-dioxabicycloctane-7-one.

7. The device of claim 1 wherein said reinforcing element is fixedly attached to said fixation component by said suture.

8. The device of claim 7 wherein said suture, said tissue scaffold component, said fixation component and said reinforcing element comprise a bioabsorbable polymer.

9. The device of claim 8 wherein said bioabsorbable polymer is selected from the group consisting of aliphatic polyesters, polyalkylene oxalates, polyamides, polycarbonates, polyorthoesters, polyoxaesters, polyamidoesters, polyanhydrides and polyphosphazenes.

* * * * *